United States Patent [19]
Harmon et al.

[11] Patent Number: 6,015,716
[45] Date of Patent: Jan. 18, 2000

[54] DETECTION OF ENDOTOXIN LEVELS IN LIPOSOMES, LIPID BILAYERS AND LIPID COMPLEXES

[75] Inventors: Paul A. Harmon, Newtown, Pa.; Donna J. Cabral-Lilly, Lawrenceville; J. Craig Franklin, Skillman, both of N.J.; Robert A. Reed, North Wales; Andrew S. Janoff, Yardley, both of Pa.

[73] Assignee: The Liposome Company, Inc., Princeton, N.J.

[21] Appl. No.: 08/679,046

[22] Filed: Jul. 12, 1996

[51] Int. Cl.[7] ............... A61K 9/50; G01N 31/00; C07F 9/02
[52] U.S. Cl. ............ 436/501; 424/283.1; 436/13; 436/829; 554/79
[58] Field of Search ............. 436/13, 501, 829; 424/283.1; 554/79

[56] References Cited

U.S. PATENT DOCUMENTS

| | | | |
|---|---|---|---|
| 4,235,871 | 11/1980 | Papahadjopoulos et al. | 424/19 |
| 4,522,803 | 6/1985 | Lenk et al. | 424/1.1 |
| 4,588,578 | 5/1986 | Fountain et al. | 424/1.1 |
| 4,810,630 | 3/1989 | Craig et al. | |
| 4,975,282 | 12/1990 | Cullis et al. | 424/450 |
| 5,008,050 | 4/1991 | Cullis et al. | 264/4.3 |
| 5,030,453 | 7/1991 | Lenk et al. | 424/450 |
| 5,169,637 | 12/1992 | Lenk et al. | 424/450 |

OTHER PUBLICATIONS

Bangham, et al., "Diffusion of Univalent Ions across the Lamellae of Swollen Phopholipids." J. Mol. Biol. 13:238 (1965).

Dijkstra et al., "Modulation of the Biological Activity of Bacterial Endotoxin By Incorporation Into Liposomes", J. Immunol, 138: 2663 (1987).

Gutierrz, et al., "Immunological methods for the detection of structural components and metabolites of bacteria and fungi in blood", Ann. Biol. Clin, 51:83 (1993).

Gruner et al., "Novel Multilayered Lipid Vesicles: Comparison of Physical Characteristics of multilamellar Liposomes and Stable Plurilamellar Vesicles", Biochemistry 24: 2833 (1985).

Hurley, "Endotoxemia: Methods of Detection and Clinical Correlates", Clin, Microbiol. Rev, 8: 268 (1995).

Kielian, et al., "CD14 and other recognition molecules for lipopolysaccharide: a review", Immunopharmacology 29: 187 (1995).

Nairn, *s Pharmaceutical Science* (A. Gennaro, ed.), Mack Publishing Co., Easton, PA (1985), 1492–1517.

Schmidtgen, et al., "Detection of Lipopolysaccharides in Phospholipids and Liposomes Using the Limulus Test", J. Liposome Research 5:109 (1995).

Trubetskoy, et al., "FITC–Labeled lipopolysaccharide: use as a probe for liposomal membrane incorporation studies", FEBS Lett. 269: 79 (1990).

Dijkstra et al "Modulation of the Biological Activity of Bacterial Endotoxin by Incorporation into Liposomes" Journal of Immunology vol. 138, 2663–2670 No. 8, 1987.

Schmidtgen et al. "Detection of Lopopolysaccharides in Phospholipids and Loposomes using Limulus Test" Journal of Liposome Research 5(1) 109–116, 1995.

Alberts et al. Molecular Biology of the Cell, 1983 pp. 255–263.

*Primary Examiner*—James C. Housel
*Assistant Examiner*—Rodney P. Swartz
*Attorney, Agent, or Firm*—Rosanne Goodman; Kenneth B. Rubin

[57] ABSTRACT

Endotoxin incorporated into liposomes, lipid bilayers or lipid complexes can be detected by combining an aqueous suspension of the liposomes, lipid complexes or lipid bilayers with a suitable detergent. Preferable detergents, e.g., Lubrol-PX™ or a polyoxyethylene ether, solubilize the lipid bilayers, liposomes or lipid complexes at acceptable lipid concentrations, forming micelles therefrom which contain lipid bilayer, liposome or lipid complex lipid, detergent and endotoxin, should it be present. The micelles are then assayed for the presence of endotoxin.

20 Claims, 3 Drawing Sheets

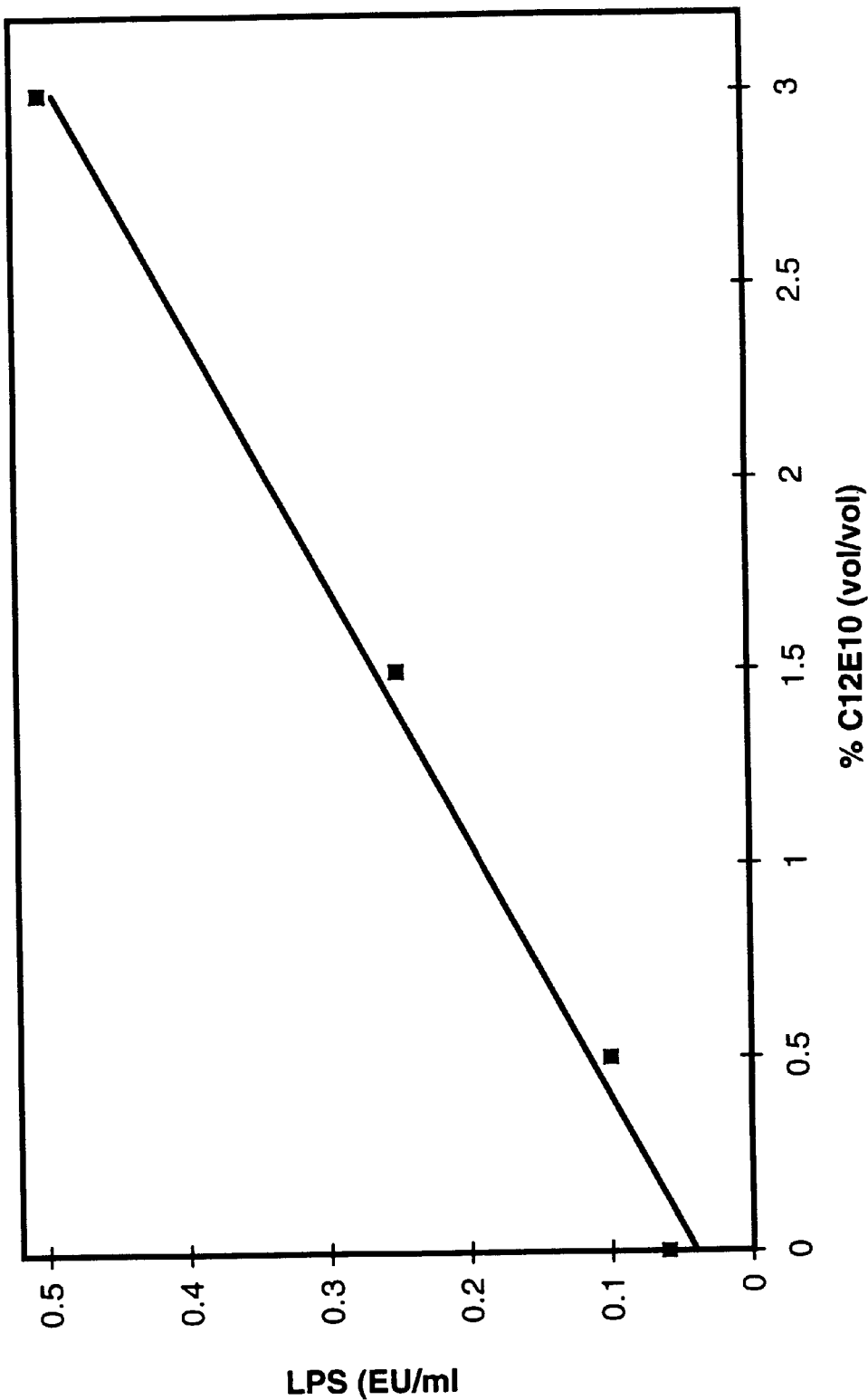

DETECTION OF ENDOTOXIN LEVELS IN LIPOSOMES, LIPID BILAYERS AND LIPID COMPLEXES

FIELD OF THE INVENTION

This invention is directed to methods of detecting the presence of endotoxin in lipid bilayers, liposomes and lipid complexes.

BACKGROUND OF THE INVENTION

Endotoxin is a lipopolysaccharide ("LPS") found in the outer membrane of most gram-negative bacteria. Endotoxin's biologically active moiety, lipid A, associates with a LPS-binding protein ("LBP") in mammals; the resultant LPS/LBP complex binds to the CD14 surface receptor on macrophages and other LPS-responsive cells (Kielian and Blecha, *Immunology* 29: 187 (1995)). Exposure to endotoxin can thereby lead to fever and leukopenia followed by leukocytis, and in larger doses, shock. Accordingly, detection and quantification of endotoxin is an important concern in the manufacture of pharmaceutical formulations. More than 20 assays for the detection of endotoxin have been reported, but an assay based on the coagulation of *Limulus polyphemus* blood is the method of choice (Hurley, *Clin. Microbiol. Rev.* 8: 268 (1995). It has the advantages of increased sensitivity, potential for quantitation, reactivity with the biologically active component, lipid A and relative convenience of operation. It makes use of endotoxin-induced activation of enzymes in the Limulus coagulation cascade; these enzymes then react with a clottable protein, forming a detectable gel that is indicative of the presence of endotoxin (the "LAL assay"; Sullivan et al., in: *Mechanisms in Bacterial Toxicology* (Bernheiner, ed.), John Wiley & Sons, NY (1976), p. 217). The LAL assay is capable of detecting endotoxin at levels as low as several picograms of endotoxin per ml of sample.

However, incorporation of endotoxin into lipid bilayers, liposomes or lipid complexes masks the lipid A moiety from LBP and assay enzymes, inhibiting the ability of assay enzymes to interact with lipid A and thereby decreasing the sensitivity of the assay (J. Dijkstra et al., *J. Immunol.* 138: 2663 (1987)). Therefore, accurate assays for the detection of endotoxin sequestered in such structures must provide a means for unmasking endotoxin's lipid A moiety. Previously known methods have proved to be inappropriate, ineffective or too inefficient to have practical use. For example, Gutierrez and Liebana, (*Ann. Biol. Clin.* 51: 83 (1993)) noted that immunological methods are expensive and insensitive. The method developed by Trubetskoy et al. (FEBS Lett. 269; 79 (1990)), based on the development of a fluorescent derivative of LPS, provided important information for understanding LPS-lipid bilayer interaction, but was unsuitable for detecting unlabeled LPS. Schmidtgen and Brandl (Journal of Liposome Research 5;109 (1995)) describe a method based on solubilization of liposomes with ethanol followed by a series of labor intensive ultrafiltration steps. This method is time consuming and expensive. An efficient method having a minimum number of steps and avoiding exposure of the sample to potentially contaminated glassware and solvents is needed.

This invention provides a method which is able to reliably, and with sufficient sensitivity, detect the presence of endotoxin in lipid bilayers, liposomes or lipid complexes. Detergents disturb the stability of lipid bilayers, liposomes and lipid complexes, thus solubilizing the structures. When present in sufficient concentrations in suspensions of lipid bilayers, liposomes or lipid complexes, detergents disrupt their structures, forming micelles therefrom which contain the detergent, lipid and lipid-soluble lipid contents of the bilayer, liposome or complex. Detergents thus solubilize the lipid bilayers, liposomes or lipid complexes. Endotoxin assays require that detergents be used at a concentration sufficient for the detergent to solubilize substantially all of the lipid bilayers, liposomes or lipid complexes present in a suspension, so that substantially all of the endotoxin present in these structures is released therefrom for detection and quantification. Solubilization of less than substantially all of the available lipid bilayers, liposomes or lipid complexes does not release substantially all of the endotoxin present, and does not lead to a reliable result when an endotoxin assay is applied to the resulting micellar suspension.

However, some detergents, when present in sufficient concentration to solubilize lipid bilayers, liposomes or lipid complexes, can also affect molecules enmeshed in these lipid-based structures other than the amphipathic lipids which are the structures' primary constituents. The structure of lipid A, for example, is affected by detergents which have previously been applied in endotoxin assays such that the assay detection means have been inhibited from interacting with the endotoxin moiety. High concentrations of such detergents thus may decrease the sensitivity of the endotoxin assays; at sufficiently high detergent concentrations, assay sensitivity is affected to a degree such that the results are not reliable.

Detergents suitable for use in the endotoxin assays of the present invention must thus be able to solubilize substantially all of the lipid bilayers, liposomes or lipid complexes present in a suspension at a detergent concentration at which detergent-mediated inhibition of the assay detection means is minimized. This invention provides an assay for detecting the presence of endotoxin in lipid bilayers, liposomes or lipid complexes, in which the detergents used can solubilize the bilayers, liposomes or complexes so as to give micellar suspensions in which the iipid concentration is at least about 1.75 mg/ml. At the same time, the detergents inhibit activity of the assay detection means by a factor of less than about 100.

No detergents previously applied to endotoxin assays meet these criteria. For example, Pyrosperse™, which is the detergent made available in connection with the LAL assay currently applied to liposomes, cannot solubilize the liposomes at the levels achieved by the detergents used in the method of this invention.

SUMMARY OF THE INVENTION

Endotoxin has a lipid A moiety that is incorporated into lipid bilayers, liposomes and lipid complexes upon their formation; lipid A is also the means by which assays detect the presence of endotoxin in these lipid-based structures. However, when lipid A is incorporated into the lipid bilayers, liposomes or lipid complexes, it is then generally unavailable for interacting with assay detection means. Accordingly, detecting the presence of endotoxin incorporated in lipid bilayers, liposomes or lipid complexes involves disrupting their structure so as to release endotoxin and make the lipid A moiety available for interaction with assay detection means.

Stable lipid bilayers, liposomes and lipid complexes are characterized by the compatible arrangement, or "packing," of their acyl chains. Agents, such as detergents, that interfere with these compatible acyl chains arrangements disturb the structural stability of the lipid bilayers, liposomes or lipid complexes and, when present in these structures at a sufficient concentration, completely disrupt them. Accordingly, lipid bilayers, liposomes or lipid complexes exposed to sufficient detergent concentrations are solubilized so as to give micelles containing the detergent, as well as the lipid, and lipid-soluble content, of the bilayers, liposomes or complexes.

Some detergents also denature proteins, resulting in reduction or loss of their activity. The enzymes involved in the coagulation cascade of Limulus polyphemus blood, and employed by the most commonly used endotoxin assay, have proved to be sensitive to small amounts of some detergents. Accordingly, detergents can interfere with the sensitivity of endotoxin detection assay. However, this invention provides an assay for endotoxins utilizing detergents which unmask and release the LPS from lipid bilayers, liposomes or lipid complexes, while minimally interfering with assay detection means, including Limulus coagulation enzymes. This invention also provides a method for identifying detergents suitable for use in assaying endotoxin in compositions, containing lipid bilayers, liposomes or lipid complexes.

Preferable detergents useful in the endotoxin assays of this invention solubilize lipid bilayers, liposomes or lipid complexes so as to achieve micellar lipid concentrations of at least about 1.75 mg/ml. Use of less preferable detergents requires that lipid bilayers, liposomes or lipid complex preparations be diluted, to reduce overall lipid concentration, prior to contacting the lipid-based structures with detergent. However, large dilution factors can decrease the sensitivity, and consequently the validity, of endotoxin assays in the eyes of regulatory agencies responsible for reviewing and approving pharmaceutical products. Accordingly, the use of large dilution factors should be avoided when making pharmaceutical products. In addition, detergents should be avoided which damage lipid A structure, as this can also decrease the sensitivity of endotoxin assays. The method of this invention provides detergents and conditions which meet these criteria.

Alternatively, this invention provides a method for using less optimal detergents without diluting the assay sample, by varying the temperature at which the lipid solubilization is carried out.

This invention's method produces micellar suspensions in which endotoxin is detectable at levels as low as 0.1 EU (endotoxin unit)/ml. Detergents used in the method inhibit endotoxin assays by a factor of no more than about 100; that is, assay enzymes have, in the presence of the detergents, at least 1% of the activity exhibited in the detergents' absence. The detergent is preferably selected from the group consisting of Lubrol-PX™ or a polyoxyethylene ether (C12EX). More preferably, the detergent is a polyoxyethylene ether having from about 6 to about 23 ethylene units, and most preferably, a polyoxyethylene ether having 10 ethylene units (i.e., polyoxyethylene 10 lauryl ether ("C12E10")).

BRIEF DESCRIPTION OF THE DRAWINGS

FIG. 1. A graphical representation of the inhibition of the LAL gel-clot assay by increasing concentrations of C12E10 detergent. Known amounts of endotoxin standard were added to the solutions, and the minimum required for a positive gel result is plotted for each detergent concentration. The data were fitted to a line using least squares regression analysis, R=0.992.

DETAILED DESCRIPTION OF THE INVENTION

Figure 2A:
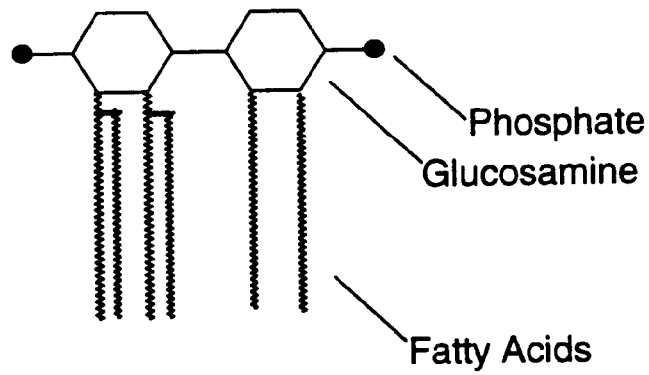
FIG. 2. Chemical Structures of Lipid A, Mutant *Salmonella Minnesota* RE595 and wild-type *Salmonella Minnesota* 595. Lipid A and mutant Salmonella are hydrophobic and readily soluble in chloroform. Wild-type Salmonella is soluble in aqueous solutions.

Following are abbreviations, and the corresponding substances designated by the abbreviations, which may be found throughout this application: EPC, egg phosphatidylcholine; DMPC, dimyristoyl phosphatidylcholine; DPPC, dipalmitoyl phosphatidylcholine; DSPC, distearoyl phosphatidylcholine; PC, phosphatidylcholine; CSE, control standard endotoxin; EU, endotoxin unit; CHOL, cholesterol; MLV, multilamellar vesicle; SPLV, stable plurilamellar vesicle; SWFI, sterile water for injection; C12E3, polyoxyethylene 3 lauryl ether; C12E4, polyoxyethylene 4 lauryl ether; C12E6, polyoxyethylene 6 lauryl ether; C12E8, polyoxyethylene 8 lauryl ether; C12E9, polyoxyethylene 9 lauryl ether; C12E10, polyoxyethylene 10 lauryl ether; C12E23, polyoxyethylene 23 lauryl ether (Brij-35); W-1, polyoxyethylene ether W-1; LUBROL-PX™, polyoxyethylene 8 cetyl ether; DOTAB, dodecyltrimethylammonium bromide; CHAPS, 3-[3-cholamidopropyl)dimethylam-monio]-1-propane sulfonate; decyl-maltoside, decyl-$\beta$-D-maltopyranoside; LAL, Limulus amebocyte lysate; LPB, lipopolysaccharide binding protein; LPS, lipopolysaccharide; LLPS liposomal LPS; Mt-LPS, mutant-LPS from *Salmonella minnesota*; octyl glucoside, octyl-$\beta$-D-glucopyranoside; TEA, triethylamine; $T_m$, temperature at which lipid changes from gel to liquid crystalline phase; wt-LPS, wild type LPS from *Salmonella minnesota* or *Escherichia coli*; and, USP, United States Pharmacopeia.

This invention provides a method of detecting the presence of endotoxin in lipid bilayers, which are lipid-based structures comprising two opposing monolayers of amphipathic lipid molecules. Such lipids have both polar headgroups and nonpolar acyl chain regions. Energetically unfavorable contacts between the acyl chains and the surrounding aqueous medium induce the lipids to arrange themselves such the chains are oriented towards the interior of the bilayer while the headgroups are oriented towards the aqueous medium.

This invention's method is also applicable to detecting the presence of endotoxin in liposomes, which are lipid-based structures having either one (unilamellar liposomes) or multiple (oligolamellar or multilamellar liposomes) lipid bilayers. Each bilayer surrounds an aqueous compartment. Unilamellar liposomes can be small liposomes ("SUVs"), i.e., have an average size between 25–50 nm, or large liposomes ("LUVs"). Liposomes can be made by a variety of methods (for a review, see, for example, Deamer and Uster (1983)). These methods include without limitation: Bangham's MLV method, involving: dissolution of a lipid in an organic solvent; removal of the solvent so as to obtain dried lipid; and then rehydration of the dried lipid with an aqueous phase, with agitation, so as to obtain liposomes (Bangham et al., J. Mol. Biol. 13: 238 (1965)). Lenk, Fountain and Cullis each describe different methods of making stable plurilamellar liposomes ("SPLVs;" see U.S. Pat. Nos. 4,522,803, 4,588,578, 5,030,453, 5,169,637 and 4,975,282). Furthermore, Paphadjopoulos (U.S. Pat. No. 4,235,871) describes a method for preparing oligolamellar liposomes by reverse-phase evaporation ("REVs"). Moreover, unilamellar liposomes can be produced from MLVs by such methods as sonication (see Papahadjopoulos et al. (1968)) and extrusion (see, for example, Cullis et al., U.S. Pat. Nos. 5,008,050). The contents of the above-cited documents are incorporated herein by reference.

Moreover, this invention's method can be applied to the detection of endotoxin in lipid complexes, which are nonliposomal, nonlamellar lipid-based structures.

Lipid bilayers, liposomes or lipid complexes assayed by the methods of this invention can comprise any lipid generally recognized as suitable for incorporation in such structures. Preferably, the lipid comprises a phospholipid, which itself is preferably a phosphatidylcholine ("PC"), e.g., egg phosphatidylcholine ("EPC"), dipalmitoyl phosphatidylcholine ("DPPC"), distearoyl phosphatidylcholine (DSPC"), pailmitoyloleoyl phosphatidylcholine ("POPC"), dioleoyl phosphatidylcholine ("DOPC"), dimyristoyl phosphatidylcholine ("DMPC") or dilauroyl phosphatidylcholine ("DLPC"). Additionally, or alternatively, when desired by ordinarily skilled artisans, the phospholipid can be a phosphatidy,serine ("PS"), phosphatidylethanolamine ("PE") or phosphatidylglycerol ("PG"). Moreover, the lipid can comprise a sterol, which is preferably cholesterol, but can also be a cholesterol derivative, e.g., cholesterol hemisuccinate, alpha-tocopherol or another sterol. The assay method of the present invention may be used for any type or composition of lipid bilayers, liposomes or lipid complexes as long as the detergent type, concentration and temperature of solubilization are adjusted, as described herein, to account for the lipid types and concentration present in the sample, as well as the type of lipid bilayer, liposome or lipid complex to be solubilized.

Lipid bilayers, liposomes or lipid complexes are solubilized herein in order to make endotoxin lipid A moieties available for interaction with the detection means of endotoxin detection assays. Detergents incorporate into such lipid-based structures, disrupting the packing of their lipid molecules and, at a sufficient concentration, causing their complete structural disruption and forming micelles as a result. "Micelles" are structures comprising a single layer of amphipathic lipid molecules, th e polar portions of which are arranged around the exterior of the micelle, and the acyl chains of which are in the micelle's interior. Detergent-formed micelles contain the detergent, endotoxin and bilayer, liposome or complex lipid, as well as their lipid-soluble contents. Micelles are assayed for endotoxin using any accepted test method for detecting the presence of lipid A in a sample, the most commonly used test being the Limulus amebocyte lysate ("LAL") assay. The LAL assay uses enzymes to coagulate the lysate in the presence of endotoxin.

Selection of a suitable detergent will depend on a number of factors well within the purview of ordinarily skilled artisans given the teachings of this invention to determine and account for. These include, without limitation: the type of lipid present in the lipid bilayer, liposome or lipid complex; the concentration of lipid in the sample; the concentration of the selected detergent necessary to solubilize the particular sample; and, the degree of inhibition of the endotoxin assay exhibited by the detergent at the required solubilizing concentration. For lipid samples which are relatively easy to solubilize, detergents with lower solubilizing capacity a re acceptable. Lipid samples requiring more stringent solubilizing conditions will require stronger detergents, a higher detergent concentration or a higher temperature during the solubilization process. Suitable solubilizing detergent conditions can then easily be tested in an endotoxin detection assay, e.g., the LAL assay, to determine if the assay retains sufficient sensitivity, i.e., sensitivity is not decreased by more than 100 fold.

Various detergents were tested to examine their ability to disrupt lipid-based structures. As representative cases, solubilization studies of EPC, DMPC, DPPC and DSPC multi-lamellar liposomes ("MLVs"), as well as their cholesterol containing analogs (40 mole percent cholesterol), were performed with the detergents listed in Table I and Table II. The maximum concentration of lipid that gave a transparent dispersion is listed in Table I for cholesterol-free liposomes, and Table II for 40 mole % cholesterol analogs.

The overall performance of a detergent's liposome-solubilizing capability was defined as the solubility index, which is the sum of the maximum lipid solubilities for each liposome dispersion. The solubility indices are listed in Tables I and II, and serve as a qualitative gauge of the detergents' liposome solubilizing effectiveness. The detergents in vestigated in this search included non-ionic, anionic, cationic and zwitterionic detergents as well as the detergent "Pyrosperse" which is sold commercially for use with the LAL Assay. The c harged detergent s, Lubrol-PX and the "C12EX" series of polyoxyethylene lauryl ethers with X>6, showed excellent liposome solubilizing properties resulting in dispersion indices greater than 35 for cholesterol-free liposomes. Tween 20 and Tween 80 were significantly less effective, while Triton X-100 provided acceptable liposome solubilization. Pyrosperse, the only detergent sold commercially specifically for use with the LAL endotoxin assay, was totally ineffective for solubilizing the liposomes investigated. In all cases examined, incorporation of cholesterol into the membrane lessened the detergents effectiveness and as a result, dispersion indices decreased.

Liposome morphology was found to affect solubilization rates. EPC/CHOL large unilamellar liposomes, MLVs and stable plurilamellar liposomes were made at 10 mg/ml total lipid, 40 mol % CHOL, and diluted into 0.5% C12E10. Although all three samples were soluble at 1.25 mg/ml in this detergent, the conditions needed were different. The unilamellar vesicles were visibly clear after vortexing at room temperature. For MLVs, heating at 37° C. for 15 min followed by vortexing for 3 min was required. The SPLV sample would not completely solubilize until it was heated for 45 sec at 60° C. and vortexed for 1 min.

The degree of inhibition of the LAL assay by detergents which showed reasonable liposome solubilizing properties was determined by performing the LAL assays on detergent solutions to which known amounts of standard wt-LPS had been added. All detergents with a dispersion index greater than about 30 were examined (Table I). Each detergent tested inhibited the LAL assay to some degree. The charged detergents CHAPS, cholate, deoxycholate and DOTAB all dramatically decreased the LAL assay sensitivity by more than a factor of 100. Similarly, the nonionic detergents octyl-glucoside, decyl maltoside and Triton X-100 also severely inhibited the LAL assay (results not shown). The remaining detergents, all belonging to the C12EX series of polyoxyethylene lauryl ethers, showed less LAL inhibition.

Table III gives the LAL detection limits for 0.5% levels of the C12EX detergents in the presence of known amounts of added endotoxin. C12E10 and C12E23 inhibited the LAL assay by only a factor of about 2 compared to detergent free solution. Curiously, while C12E10 and C12E23 showed the same two-fold inhibition, progressively shortening the ether repeat number (X) from 10 to 6 led to systematic increases in LAL inhibition. C12E6 inhibited the LAL assay by a factor of 42 at the 0.5% detergent level. FIG. 1 shows the LAL detection limit for C12E10 at increasing detergent concentrations.

The detection limit is better at lower detergent concentrations, but the amount of lipid dissolved is also lower. At the 1.5 or 3.0% detergent levels required for solubilization of 10–20 mg/ml lipid dispersions, C12E10 inhibited the LAL assay by an additional factor of 2 or 4. In contrast, C12E23 inhibited the LAL assay by an additional factor of at least 64 at these higher levels (data not shown). Therefore, we identified C12E10 as the most preferred candidate for release and quantification of liposomal endotoxin since it inhibited the LAL assay the least and provided excellent liposome solubilization. In fact, the detergent inhibition could be partially overcome by increasing the incubation time for the LAL test from 60 min to 120 min at 37° C. All negative controls (SWFI or detergent alone) were still negative after 120 min, and standard dilutions curves for CSE gave similar results at 60 and 120 min.

Heating was required to solubilize some of the lipid samples prior to performing the endotoxin assay. No inhibition of LAL sensitivity was found for any sample whe n heated to $\leq 37°$ C. Incubating samples at temperatures greater than 37° C. for sustained periods of time resulted in loss of LAL sensitivity (e.g. see Table III) and inconsistent detection. It was possible, however, to apply short bursts of high heat ($\leq 45$ sec at 65° C.) to solubilize liposomal formulations not dissolved at 37° C. and not interfere with the LAL assay.

Once all lipid bilayer, liposome or lipid complex structures are completely disrupted by a detergent, preferably C12E10, the endotoxin detection limit is determined only by the LAL inhibition from the detergent and the micellar lipid. Because 0.5% C12E10 gave the least inhibition of the LAL assay, we determined the endotoxin detection limits for PC and PO/CHOL MLVs at this detergent concentration. The solubility or dispersion limits for each liposome preparation were found by successive heating and dilution as described in Example 3 for endotoxin limits. These limits or index are shown in Tables I and II. Heating to 37° C. followed by vortexing was sufficient to solubilize all but the DSPC-containing MLVs. A 30 sec incubation at 65° C. was needed for the DSPC samples. EPC liposomes had a lower solubility (2.4 mg/ml) than the other PC liposomes (4 mg/ml). In the presence of 40 mol % chole sterol, the dispersion limit for all samples was 1.25 mg/ml.

Table V also shows the endotoxin detection limits, defined as the minimum amount of CSE needed in the final diluted, clear sample to give a positive LAL test. Note that CSE was added before the heating/dilution cycle to mimic conditions needed for p ractical testing for LPS contamination during liposomal preparation. The detection limit for DSPC was not significantly different from that of 0.5% C12E10 alone. The presence of EPC or DPPC increased the limit ~3-fold. Remarkably, DMPC at 4 mg/ml had a dramatic inhibitory affect on the LAL assay with a 60-fold decrease in sensitivity. In the absence of DMPC, the presence of CHOL had little affect on the detection limit once the sample was solubilized. The improved detection limit for DMPC/CHOL may reflect the much smaller amount of DMPC in this sample (0.96 mg/ml).

LPS was also incorporated into EPC and DSPC SPLVs, by adding CSE to the buffer/solvent mixture before the solvent was removed. Two CSE levels were used, corresponding to 1x or 10x the endotoxin detection limit for MLVs of these phospholipids given in Table V. Complete masking of the LPS occurred at both CSE levels for both PCs. This result is analogous to the lipid A masking in EPC MLVs. After solubilization of the SPLVs, however, the endotoxin detection limits were the same as those found for the MLVs. "Solubilization" of lipid bilayers, liposomes or lipid complexes by detergent according to the practice of this invention means complete, or substantially complete, conversion of the bilayer, liposomal or complex lipid to micellar lipid. Such conversion is generally accompanied by a decrease in the turbidity of the accompanying aqueous medium, and can be observed by ordinarily skilled artisans. Accordingly, the amount of detergent used in the method of this invention is an amount sufficient to substantially solubilize the lipid-based structure being assayed. The detergents inhibit endotoxin assays by a factor of no more than about 100, that is, the assay detection means in the presence of the detergents retain at least about 1% of the activity exhibited in the absence of detergent. Preferably, the detergents inhibit endotoxin assays by a factor of no more than about 50, more preferably by a factor of no more than about 10, still more preferably, by a factor of no more than about 2.5, and most preferably, by a factor of no more than about 1.

Detergents, e.g., polyoxyethylenes or Lubrol-PX™, particularly useful in the method of this invention solubilize lipid bilayers, liposomes or lipid complexes so as to give at least a 1.75 mg/ml lipid concentration in the resulting micellar suspension. Preferably, in order to avoid the need to dilute preparations, the detergents give at least a 4 mg/ml lipid concentration. Preferably, the detergent is a polyoxyethylene detergent. These can be designated by the formula "C12EX," wherein "X" is an integer equal to the number of ethylene units in the detergent. More preferably, the detergent is a polyoxyethylene detergent having from 6 to 23 ethylene units, i.e., C2E6 to C12E23. Most preferably, the detergent is polyoxyethylene 10 lauryl ether, C12E10, which is available from Sigma Chemical Co. (St. Louis, Mo.).

Endotoxin levels as low as about 0.1 EU of endotoxin per ml of sample can be detected using the methods of this invention.

Lipid bilayers, liposomes or lipid complexes assayed by this invention's method are typically suspended in "pharmaceutically acceptable carriers," which are media generally acceptable for use in connection with the administration of such structures to animals, including humans. Pharmaceutically acceptable carriers are generally formulated according to a number of factors (see, for example, Nairn, in: *Reminaton's Pharmaceutical Science* (A. Gennaro, ed.), Mack Publishing Co., Easton, Pa., (1985), pp.1492–1517) well within the purview of the ordinarily skilled artisan to determine and account for. Such factors include, without limitation: the particular bioactive agent incorporated in a lipid bilayer, liposome or lipid complex, as well as its concentration, stability and intended bioavailability; the disease, disorder or condition being treated with a composition; the subject, its age, size and general condition; and the composition's intended route of administration, e.g., nasal, oral, ophthalmic, topical, transdermal, vaginal, subcutaneous, intramammary, intraperitoneal, intravenous, or intramuscular. Pharmaceutically acceptable carriers can contain additional ingredients, for example those which enhance the stability of the active ingredients included, such as preservatives and anti-oxidants. Typical pharmaceutically acceptable carriers used in connection with lipid bilayers, liposomes and lipid complexes include, for example, D5W, an aqueous solution containing 5% weight by volume of dextrose, and physiological saline.

Liposomes, lipid bilayers or lipid complexes assayed by the methods of this invention can comprise one or more "biologically active (or bioactive)" agents, which are any compound or composition of matter that can be administered to animals, preferably humans. Bioactive agents have biological activity in animals, and can be used therapeutically or diagnostically. Bioactive agents which may be associated with lipid bilayers, liposomes or lipid complexes include, but are not limited to: antiviral agents such as acyclovir, zidovudine and the interferons; antibacterial agents such as aminoglycosides, cephalosporins and tetracyclines; antifungal agents such as polyene antibiotics, imidazoles and triazoles; antimetabolic agents such as folic acid, and purine and pyrimidine analogs; antineoplastic agents such as the anthracycline antibiotics and plant alkaloids; sterols such as cholesterol; carbohydrates, e.g., sugars and starches; amino acids, peptides, proteins such as cell receptor proteins, immunoglobulins, enzymes, hormones, neurotransmitters and glycoproteins; dyes; radiolabels such as radioisotopes and radioisotope-labeled compounds; radiopaque compounds; fluorescent compounds; mydriatic compounds; bronchodilators; local anesthetics; and the like.

This invention will be better understood from the following Examples, but is not limited thereby. Those of ordinary skill in the relevant art will readily understand that the Examples are merely illustrative of the invention as fully defined in the claims which follow thereafter.

EXAMPLES

Example 1

Materials

DMPC, DPPC and DSPC were purchased from Nippon Oil & Fats Co., LTD (Amagasaki, Japan) and Avanti Polar Lipids (Alabaster, Ala.). EPC was purchased from LIPOID KG (Ludwigshafen, Germany) and Avanti. All phospholipids were used without further purification. Cholesterol, C12E3, C12E4, C12E6, C12E8, C12E9, C12E10, C12E23, W-1, CHAPS, DOTAB, Triton X-100 and Tween-80 were purchased from Sigma (St. Louis, Mo.). C12E8, C12E9, Lubrol PX™ (10% solution, Protein Grade), octylglucoside, decyl-maltoside, deoxycholate, cholate, and Tween-20 were purchased from CalBiochem (San Diego, Calif.).

Pyrosperse™ (40% solution) was obtained from BioWhittaker, Inc. (Walkersville, Md.). Salmonella minnesota Lipid A and Mt-LPS (Re595) were purchased from LIST Biologicals (Campbell, Calif.). Wt-LPS was obtained from either Endosafe, Inc. (E. coli 055:B5, Charleston, S.C.), United States Pharmacopeia (E. coli 055:B5, Rockville, Md.) or LIST Biologicals (Salmonella minnesota, Campbell, Calif.), and control standard endotoxin (CSE) from Associates of Cape Cod (Woods Hole, MA). Sterile water for injection (SWFI) and 0.9% saline for injection were purchased from Abbott Laboratories (Chicago, Ill.). Limulus amebocyte lysate reagent, 0.06 EU/ml sensitivity, was purchased from Endosafe, Inc or Associates of Cape Cod.

A commercial endotoxin removal syringe tip (Pyrobind, Sepracor Inc., Marlborough, Mass.) was used to pretreat detergent solutions to assure the absence of endotoxin contamination. All detergent solutions where adjusted to neutral pH. All other chemicals were used as received. All glassware used for liposome preparation was depyrogenated by heating for at least three hours at 250° C. Liposome samples were then placed in sterile, pyrogen-free polystyrene tubes for all further studies.

Example 2

Liposome Preparation

MLVs comprised of EPC, DMPC, DSPC and DPPC were prepared by drying appropriate lipid, obtained as described above, and cholesterol from chloroform solutions on a rotoevaporator, and then further drying for several hours under high vacuum. PC/CHOL samples were at a 60:40 mol ratio. The resulting film was hydrated with 0.9% sterile saline solution by heating the dispersion at least 10° C. above the target liposome $T_m$ for 1 hour with intermittent vortexing.

EPC was used for incorporation studies of LPS in MLVs, the results of which are show n in Table III (see below). EPC MLVs containing Lipid A or MT-LPS were made by simply premixing desired amounts of EPC and Lipid A or MT-LPS chloroform solutions. Chloroform was then removed by rotoevaporation and drying under vacuum for at least three hours. The EPC/Lipid A or MT-LPS film was then resuspended in pyrogen free saline. wt-LPS is not soluble in lipid casting solvents, and was incorporated into liposomes by hydra ting dry EPC with saline containing the desired amounts of wt-LPS.

The dispersion was then dried by rotoevaporation at 45 degrees, and resuspended in SWFI, then dried and resuspended in SWFI one final time. This method is similar to the "dry method" (Dijkstra et al.) for wt-LPS incorporation except for the one minute sonication periods which we have omitted. Liposomes were washed by repeated pelleting by centrifugation and resuspension in fresh SWFI. SPLVs of DSPC, EPC or EPC/CHOL were made by a modification of the method of Gruner et al. (Biochemistty 24: 2833 (1985)). To incorporate endotoxin, CSE was added to the buffer phase before solvent removal. The contents of the above-cited documents are i ncorpora ted herein by reference Example 3

Detergent-Mediated Solubilization of Lid osomal Dispersions

Quantitative detergent-mediated solubilization was determined by adding a volume of detergent to a 20 mg/ml MLV suspension, prepared as described above, to give 14 mg/ml lipid in 1.5% detergent (vol./vol.). The mixture was then vortexed well and heated at 65° C. for 20 minutes, following which it was allowed to sit at room temperature for 1 hour. A one-hour time frame was chosen to assure that the lipid remained solubilized throughout the LAL assay. Solutions that appeared visually transparent at the end of this hour were considered "solubilized." All dispersions that were not clear were subsequently diluted by a factor of two in 1.5% detergent, reheated, cooled and then reexamined.

As representative cases, studies on EPs, DMPC, DPPC and DSPC MLVs, as well as their cholesterol-containing analogs (40 mole percent cholesterol), were performed with the detergents listed in Tables I and II (see below). The maximum concentration of lipid that gave a transparent solution is listed in Table I for cholesterol free liposomes, and in Table h1 for 40 mole % cholesterol-containing analogs.

The overall performance of a detergent's ability to convert liposomes to visually clear solutions was defined as the solubility index, which is simply a sum of the maximum lipid concentration which could be "solubilized" at the indicated detergent concentration. The solubility indices are listed in Tables I and II, and serve as a qualitative gauge of the detergents' effectiveness. The detergents investigated in this search included non-ionic, anionic, cationic and zwitterionic detergents as well as the detergent Pyrosperse™ which is sold commercially for use with the LAL Assay.

The charged detergents, Lubrol-PX™ and the "C12EX" series of polyoxyethylene lauryl ethers with X>6 showed excellent liposome solubilizing properties, resulting in solubility indices greater than 35 for cholesterol-free liposomes. Tween 20 and Tween 80 were significantly less effective, while Triton X-100 provided acceptable liposome solubilization. It is interesting to note that s, the only detergent sold commercially specifically for use with the LAL endotoxin assay, was totally ineffective for solubilizing the liposomes investigated.

In all cases examined, incorporation of cholesterol into the membrane lessened the detergents' effectiveness and as a result, solubility indices decreased. The morphology of the liposome also affected its rate of solubilization. EPC/CHOL large unilamellar vesicles, MLVs and SPLVs were made at 10 mg/ml total lipid, 40 mol % CHOL, and diluted into 0.5% C12E10. Although all three samples were soluble at 1.25 mg/ml in this detergent, the conditions needed were different. The unilamellar vesicles were visibly clear after vortexing at room temperature. For MLVs, heating at 37° C. for 15 min followed by vortexing for 3 min was required. The SPLV sample would not completely solubilize until it was heated for 45 sec at 60° C. and vortexed for 1 min.

TABLE I

QUALITATIVE DETERGENT SOLUBILIZATION OF NON-CHOLESTEROL CONTAINING LIPOSOMES
(maximum MLV lipid concentration solubilized at the indicated detergent levels, mg/ml)

| Liposomal Lipid > Detergent | EPC | DMPC | DPPC | DSPC | Solubility Index |
|---|---|---|---|---|---|
| nonionic | | | | | |
| 1.5% Tween-20 | -a- | 3.50 | 3.50 | 1.75 | 8.75 |
| 1.5% Tween-80 | -a- | 1.75 | 1.75 | -a- | 3.50 |
| 1.5% Triton X-100 | 3.50 | 14.00 | 14.00 | -a- | 31.50 |
| 1.5% Octyl-glucoside | 7.00 | 14.00 | 14.00 | 7.00 | 42.00 |
| 1.5% Decyl-maltoside | 7.00 | 14.00 | 14.00 | 7.00 | 42.00 |
| 1.5% Lubrol-PX ™ | 7.00 | 14.00 | 14.00 | 7.00 | 42.00 |
| 1.5% W-1 | 1.75 | 7.00 | 3.50 | 3.50 | 15.70 |
| 1.5% C16E8 | 1.75 | 3.50 | 1.75 | 1.75 | 8.70 |
| C12E3[b] | ** | ** | ** | ** | ** |
| C12E4[b] | ** | ** | ** | ** | ** |
| 1.5% C12E6 | 3.50 | 3.50 | 3.50 | 1.75 | 12.20 |
| 1.5% C12E8 | 7.00 | 14.00 | 14.00 | 7.00 | 42.00 |
| 1.5% C12E9 | 7.00 | 14.00 | 14.00 | 14.00 | 49.00 |
| 1.5% C12E10 | 7.00 | 14.00 | 14.00 | 14.00 | 49.00 |
| 1.5% C12E23 (Brij-35) | 1.75 | 14.00 | 14.00 | 7.00 | 36.70 |
| zwitterionic | | | | | |
| 1.5% CHAPS | 7.00 | 14.00 | 14.00 | -a- | 35.00 |
| anionic | | | | | |
| 1.5% Cholate | 7.00 | 14.00 | 14.00 | 14.00 | 49.00 |
| 1.5% Deoxycholate | 14.00 | 14.00 | 14.00 | 7.00 | 49.00 |
| cationic | | | | | |
| 1.5% DOTAB | 7.00 | 14.00 | 14.00 | 14.00 | 49.00 |
| commercial LAL detergent | | | | | |
| 6.6% Pyrosperse ™ | -a- | -a- | -a- | -a- | | a. Liposome is solubilized at less than 1.75 mg/ml levels for the indicated detergent concentration.
[b]Aqueous solutions of these detergents could not be made at significant concentration (i.e. 0.5% or greater) levels.

TABLE II

QUALITATIVE DETERGENT SOLUBILIZATION OF CHOLESTEROL CONTAINING LIPOSOMES
(maximum MLV lipid concentration solubilized at the indicated detergent levels, mg/ml)

| Liposome -> Detergent | EPC/ CHOL | DMPC/ CHOL | DPPC/ CHOL | DSPC/ CHOL | Solubility Index |
|---|---|---|---|---|---|
| nonionic | | | | | |
| 1.5% Tween-20 | -a- | -a- | -a- | -a- | 0.00 |
| 1.5% Tween-80 | -a- | -a- | -a- | -a- | 0.00 |
| 1.5% Triton X-100 | 1.75 | -a- | -a- | -a- | 1.75 |
| 1.5% Octyl-glucoside | 7.00 | 3.50 | 3.50 | 1.75 | 15.75 |
| 1.5% Decyl-maltoside | 1.75 | 1.75 | 1.75 | 1.75 | 7.00 |
| 1.5% Lubrol-PX ™ | 3.50 | 3.50 | 3.50 | 3.50 | 14.00 |

TABLE II-continued

QUALITATIVE DETERGENT SOLUBILIZATION OF CHOLESTEROL CONTAINING LIPOSOMES
(maximum MLV lipid concentration solubilized at the indicated detergent levels, mg/ml)

| Liposome -> Detergent | EPC/ CHOL | DMPC/ CHOL | DPPC/ CHOL | DSPC/ CHOL | Solubility Index |
|---|---|---|---|---|---|
| 1.5% W-1 | 1.75 | -a- | -a- | -a- | 1.75 |
| 1.5% C16E8 | -a- | -a- | -a- | 3.50 | 3.50 |
| C12E3[b] | ** | ** | ** | ** | |
| C12E4[b] | ** | ** | ** | ** | |
| 1.5% C12E6 | 3.50 | 3.50 | -a- | -a- | 7.00 |
| 1.5% C12E8 | 3.50 | 3.50 | 1.75 | 1.75 | 10.50 |
| 1.5% C12E9 | 3.50 | 1.75 | 1.75 | 1.75 | 8.75 |
| 1.5% C12E10 | 7.00 | 3.50 | 1.75 | 1.75 | 14.00 |
| 1.5% C12E23 (Brij-35) | -a- | -a- | -a- | -a- | 0.00 |
| zwitterionic | | | | | |
| 1.5% CHAPS | -a- | -a- | -a- | -a- | 0.00 |
| anionic | | | | | |
| 1.5% Cholate | -a- | -a- | -a- | -a- | 0.00 |
| 1.5% Deoxycholate | -a- | 1.75 | -a- | -a- | 1.75 |
| cationic | | | | | |
| 1.5% DOTAB | -a- | 3.50 | -a- | -a- | 3.50 |
| commercial LAL detergent | | | | | |
| 6.6% Pyrosperse ™ | -a- | -a- | -a- | -a- | 0.00 | a. Liposome is solubilized at less than 1.75 mg/ml levels for the indicated detergent conoentration.
[b]Aqueous solutions of these detergents could not be made at significant concentration (i.e. 0.5% or greater) levels.

Example 4
LAL Assay

Limulus amebocyte lysate gel-clot assays were performed, as directed by the supplier, by adding 200 μl of sample to LAL reagent tubes (0.06 EU/ml sensitivity) and mixing. The reagent tubes were immediately incubated at 37° C. for one or two hours. Formation of a clot that was stable to careful 180 degree inversion was considered a positive response, i.e., that there was greater than 0.06 EU/ml of endotoxin.

All concentrations were calculated in EU/ml to compensate for variations in both LPS and LAL activity. The amount of endotoxin was estimated by performing successive two-fold dilutions until a stable clot failed to form. The extent of inhibition due to detergent or lipid present was determined by adding known amounts of endotoxin standard to appropriate solutions, and then measuring the sensitivity of the assay.

Heat-inactivation of LPS was investigated by heating samples at temperatures between 37° C. and 65° C. for various times before performing the LAL assay.

Example 5
Relative Detergent-Mediated Assay inhibition

The degree of inhibition of the LAL assay by detergents which showed reasonable liposome solubilizing properties was determined by performing the LAL assays on detergent solutions to which known amounts of standard wt-LPS had been added. All detergents with a solubility index greater than about 30 were examined (Table I). Each detergent tested inhibited the LAL assay to some degree. The charged detergents CHAPS, cholate, deoxycholate and DOTAB all dramatically decreased the LAL assay sensitivity by more than a factor of 100. Similarly, the nonionic detergents octyl-glucoside, decylmaltoside and Triton X-100 also severely inhibited the LAL assay (results not shown). The remaining detergents, all belonging to the C12EX series of polyoxyethylene lauryl ethers, showed less LAL inhibition.

Table III (see below) gives the LAL detection limits for 0.5% levels of the C12EX detergents in the presence of known amounts of added endotoxin. C12E10 and C12E23 inhibited the LAL assay by only a factor of about 2, compared to detergent free solution. Progressively shortening the ether repeat number (X) from 10 to 6 led to systematic increases in LAL inhibition; C12E6, for example, inhibited the LAL assay by a factor of 42 at the 0.5% detergent level.

FIG. 1 shows the LAL detection limit for C12E10 at increasing detergent concentrations. The detection limit is better at lower detergent concentrations, but the amount of lipid dissolved is also lower. At the 1.5 or 3.0% detergent levels required for solubilization of 10–20 mg/ml lipid dispersions, C12E10 inhibited the LAL assay by an additional factor of 2 or 4. Detergent inhibition could be partially overcome by increasing the incubation time for the LAL test from 60 min to 120 min at 37° C. All negative controls (SWFI or detergent alone) were still negative after 120 min, and standard dilutions curves for CSE gave similar results at 60 and 120 min.

Heating was required to solubilize some of the lipid samples prior to performing the endotoxin assay. No inhibition of LAL sensitivity was found for any sample when heated to $\leq 37°$ C. Incubating samples at temperatures greater than 37° C. for sustained periods of time resulted in loss of LAL sensitivity (see Table III) and inconsistent detection. It was possible, however, to apply short bursts of high heat ($\leq 45$ sec at 65° C.) to solubilize liposomal formulations not dissolved at 37° C., and not interfere with the LAL assay.

TABLE III

Detergent Inhibition of LAL Gel-Clot Assay[a]

| Detergent Type (0.5% by vol) | Endotoxin detection limit (EU/ml, wt-LPS) |
|---|---|
| None | 0.06 |
| C12E10 | 0.10 |
| C12E23 | 0.12 |
| Lubrol-PX ™ | 0.33 |
| C12E9 | 0.68 |
| C12E8 | 1.3 |
| C12E6 | 2.5 |
| C12E10[b] | 0.20 |

[a]All other detergents tested inhibited the LAL assay greater than 100 fold, or had solubility indices of less than 30.
[b]Sample heated to 65° C. for 4 min.

Example 6
Masking and Release of Endotoxin from Liposomes

Lipid A was incorporated into EPC MLVs to give 48,000 EU/ml Lipid A and 10 mg/ml EPC. An aliquot of these liposomes was serially diluted in pyrogen free saline and LAL tested. The liposomes tested LAL positive until a dilution factor of about 20. C12E10 was then added to each dilution to give a concentration of 1.5%, converting the liposomes to micelles. Each dilution was then LAL tested. Even with the 4-fold loss in LAL sensitivity expected from the presence 1.5% C12E10, LAL activity was observed until a total dilution factor of 160,000. The use of the detergent increased the sensitivity by a factor greater than 8000. This demonstrates endotoxin release and detection upon bilayer disruption. As a control, an identical quantity of Lipid A in chloroform was added to an empty flask, dried, and rehydrated in 10 ml of a saline solution with 0.5% TEA added to solubilize the Lipid A. For this Lipid A control (no liposomes or detergent) the LAL sensitivity is the standard 0.06 EU/ml, and LAL activity was found until a dilution factor of 800,000.

Table IV (see below) shows the Lipid A results, as well as data from similar studies of somewhat less hydrophobic Mt-LPS and hydrophilic wt-LPS. Data is also shown for incorporation experiments starting with 4800 EU/ml, 480 EU/ml, 48 EU/ml and 4.8 EU/ml levels of Lipid A. All LAL results are expressed in terms of EU/ml as described above. Column I shows the result of the wt-LPS, Mt-LPS, and Lipid A in the absence of liposomes or detergent. Column II shows the LAL activity in the presence of intact liposomes. Column III gives the LAL results after repeated washing of the liposomes with pyrogen free saline. Column IV shows the release of masked endotoxin from the washed liposomes by C12E10 solubilization. The large increases in the levels of detected endotoxin in Column IV compared to Column III demonstrate the success of the unmasking protocol. In Column V, we have estimated the approximate percentage of the LPS which was initially incorporated into the EPC liposomes. The values in Column V are calculated by the following formula:

$$\% \text{ masked LPS} = \frac{\text{total LPS added} - \text{LPS detected in intact liposome}}{\text{total LPS added}} \times 100$$

$$= \frac{\text{Column 1} - \text{column 2}}{\text{column 1}} \times 100$$

TABLE IV

INCORPORATION, MASKING AND RELEASE OF ENDOTOXIN IN EPC MLVs

| | I<br>Initial LAL Activity of Endotoxin Added to Lipid, (EU/ml) | II<br>Intact Liposomes (EU/ml) | III<br>Pyrogen-Free, Saline-Washed Liposomes, (EU/ml) | IV<br>C12E10-Solubilized, Washed Liposomes (EU/ml) | V<br>Approximate Percentage of Endotoxin Initially Masked by Liposomes |
|---|---|---|---|---|---|
| wild-type LPS | <1,200,000 | 1,200,000 | 1,200 | 480,000 | — |
| mutant LPS | 480,000 | 6,000 | 6,000 | 400,000 | <80% |
| Lipid A | 48,000 | 1 | 0–0.6 | 40,000 | <90% |
| | 4,800 | 1 | 0–0.6 | 4,000 | <90% |
| | 480 | 1 | 0 | 400 | <90% |
| | 48 | 1 | 0 | 40 | <90% |
| | 4.8 | 1 | 0 | 4 | <70% |

Figure 2B:
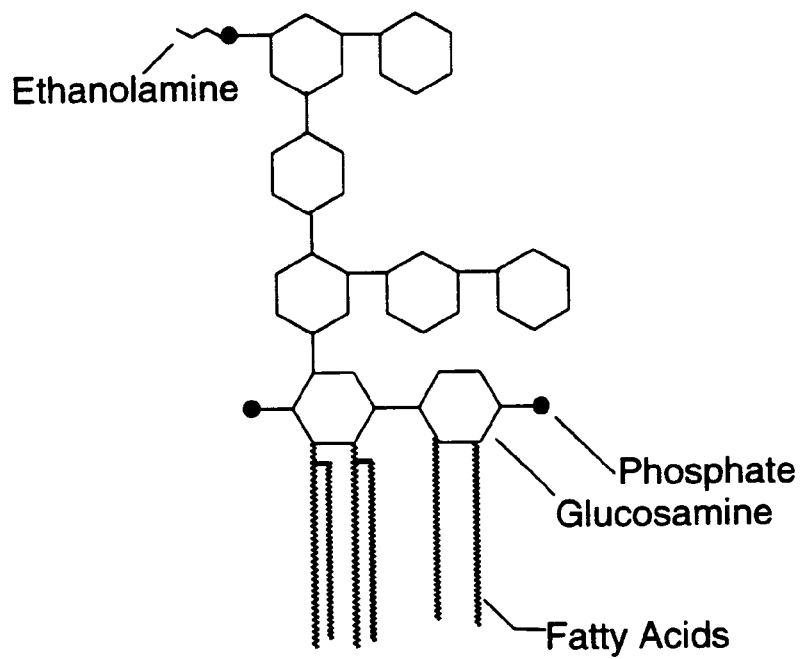
Figure 2C:
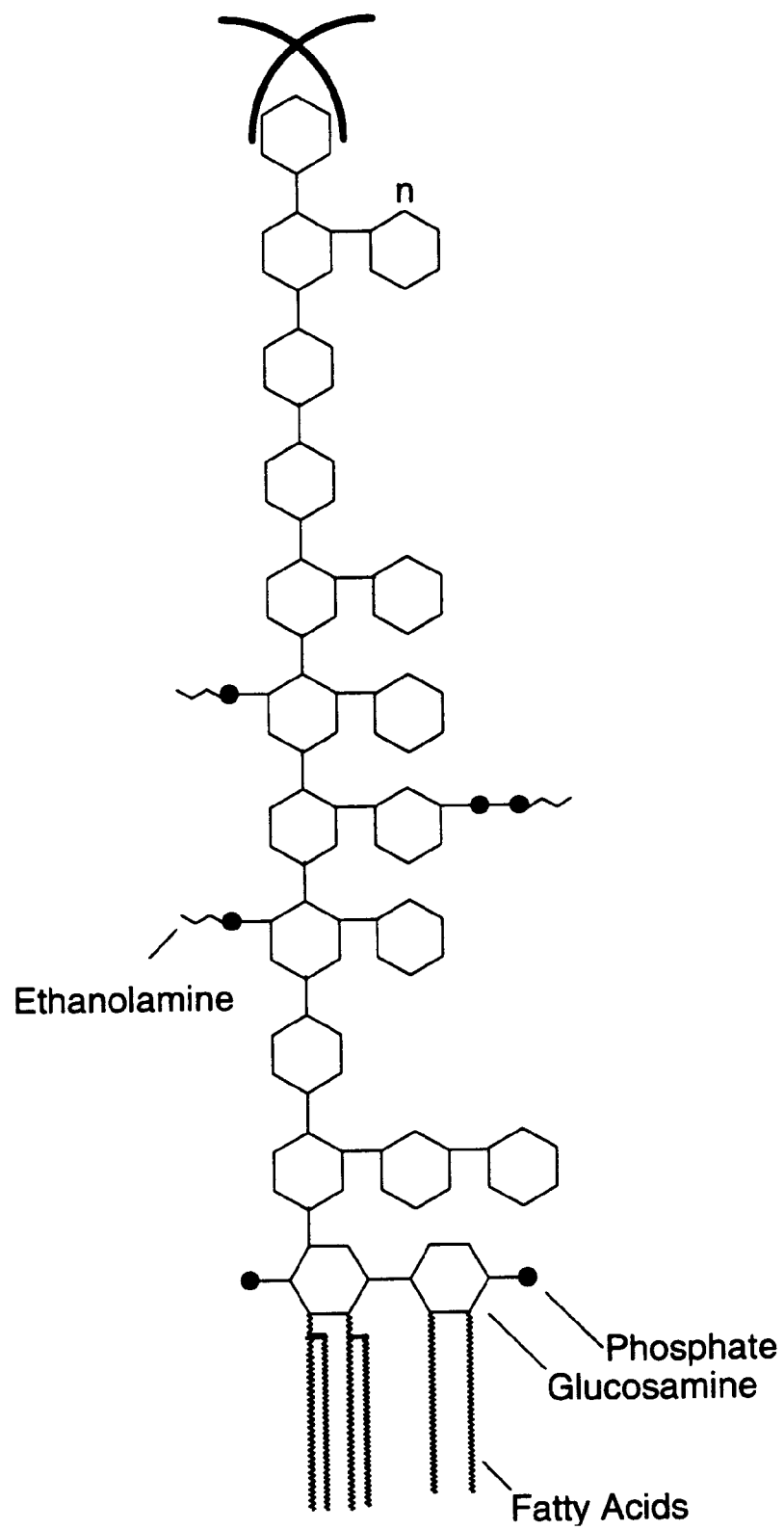

Clearly, the percentage of the initial endotoxin that actually gets inserted into the EPC bilayers is very different for wt-LPS verses Mt-LPS or Lipid A. The ease of liposomal incorporation is related to the relative hydrophobicity of the endotoxins, which is diminished as the length of the polysaccharide chain increases as shown in FIG. 2. For Mt-LPS and Lipid A incorporated at 48,000 EU/ml or greater, 90% or more of the endotoxin is undetectable by the LAL assay. The incorporation efficiency of lipid A into EPC MLVs drops to ~70% if less than 5 EU of lipid A are initially added. wt-LPS shows much less incorporation using the procedures described here for MLVs, and demonstrates the hydrophilicity of wt-LPS.

Example 7

Endotoxin Detection Limits

Once all bilayer structures are completely disrupted by C12E10, the endotoxin detection limit is determined by the LAL inhibition from the detergent and the micellar lipid. Because 0.5% C12E10 gave the least inhibition of the LAL assay, we determined the endotoxin detection limits for the PC and PC/CHOL MLVs at this detergent concentration. The liposomes were prepared as described above.

Small amounts of CSE (1×–10× the detection limit in detergent) were added to the MLVs. A minimal amount of 10% C12E10 was added to give a final detergent concentration of 0.5%. The samples were vortexed, then heated to 37° C. for 30 min. If the sample was not clear to the eye, it was diluted 2-fold in 0.5% C12E10, then reheated and vortexed. This dilution/heat cycle was repeated until the sample was clear or until the LAL assay detection limit in 0.5% detergent was reached (0.1 EU/ml). Samples still not clear were then heated for 30–45 sec at 65° C. and vortexed. All samples were clear after this treatment.

The concentration of lipid in the visually clear solution was defined as the solubility limit of the lipid in 0.5% C12E10. LAL assays were performed for each PC and PC/CHOL sample. The endotoxin detection limit was taken to be the lowest amount of CSE giving a positive LAL gel-clot result at the solubility limit. These limits are shown in Table V:

TABLE V

ENDOTOXIN DETECTION LIMITS

| Lipid | Solubility Limit of Lipid (mg/ml)[a] | LAL Detection Limit (EU/ml, CSE)[b] |
|---|---|---|
| EPC | 2.4 | 0.3 |
| DMPC | 4.0 | 6.0 |
| DPPC | 4.0 | 0.3 |
| DSPC | 4.0 | 0.1 |
| EPC/CHOL | 1.25[c] | 0.3 |
| DMPC/CHOL | 1.25[c] | 1.2 |
| DPPC/CHOL | 1.25[c] | 0.1 |
| DSPC/CHOL | 1.25[c] | 0.1 |

[a]Solubility of lipid in 0.5% C12E10.
[b]Detection limit determined at the solubility limit.
[c]Total lipid concentration (PC + CHOL) at 40 mol % CHOL.

Heating to 37° C. followed by vortexing was sufficient to solubilize all but the DSPC-containing MLVs, which required a 30-second incubation at 65° C. EPC liposomes had a lower solubility (2.4 mg/ml) than the other PC liposomes (4 mg/ml). In the presence of 40 mol % cholesterol, the solubility limit for all samples was 1.25 mg/ml. Table V also shows the endotoxin detection limits, defined as the minimum amount of CSE needed in the final diluted, clear sample to give a positive LAL test. Note that CSE was added before the heating/dilution cycle to mimic conditions needed for practical testing for LPS contamination during liposomal preparation.

The detection limit for DSPC was not significantly different from that of 0.5% C12E10 alone. The presence of EPC or DPPC increased the limit ~3-fold. Remarkably, DMPC at 4 mg/ml had a dramatic inhibitory affect on the LAL assay with a 600-fold decrease in sensitivity. The presence of CHOL had little affect on the detection limit once the sample was solubilized. The improved detection limit for DMPC/CHOL may reflect the much smaller amount of DMPC in this sample (0.96 mg/ml).

LPS was also incorporated into EPC and DSPC SPLVs, by adding CSE to the buffer/solvent mixture before the solvent was removed. Two CSE levels were used, corresponding to 1× or 10× the endotoxin detection limit for MLVs of these phospholipids given in Table V. Complete masking of the LPS occurred at both CSE levels for both PCs. This result is analogous to the LPS masking in EPC MLVs. After solubilization of the SPLVs, however, the endotoxin detection limits were the same as those found for the MLVs.

The above description of this invention is directed primarily to the preferred embodiments and practices thereof. It will be readily apparent to those skilled in the art that further changes and modifications in the actual implementation of the concepts described herein can easily be made without departing from the spirit and scope of the invention as defined by the following claims.

What is claimed is:

1. A method of detecting endotoxin in lipid complexes, lipid bilayers or liposomes, the method comprising the steps of:

(a) preparing an aqueous suspension of micelles from an aqueous suspension of lipid bilayers, liposomes or lipid complexes comprising a lipid by completely solubilizing the lipid bilayer, liposome or lipid complex suspension with a detergent so as to form micelles comprising the lipid and the detergent;

(b) assaying the micellar suspension for the presence of endotoxin, wherein, the detergent does not inhibit the endotoxin assay by a factor of more than about 100 and wherein the endotoxin assay is effective to detect endotoxin in the micellar suspension at an endotoxin concentration as low as about 0.1 EU/ml.

2. The method of claim 1, wherein the concentration of the lipid in the micellar suspension is at least 1.75 mg/ml.

3. The method of claim 1, wherein the lipid comprises a phosphatidylcholine.

4. The method of claim 3, wherein the phosphatidylcholine is selected from the group consisting of egg phosphatidylcholine, dimyristoyl phosphatidylcholine, dipalmitoyl phosphatidylcholine, distearoyl phosphatidylcholine, palmitoyloleoyl phosphatidylcholine and dioleoyl phosphatidylcholine.

5. The method of claim 1, wherein the lipid has two acyl chains and wherein each of the acyl chains is at least 16 carbon atoms in length.

6. The method of claim 5, wherein each of the acyl chains is about 18 carbon atoms in length.

7. The method of claim 1, wherein the lipid comprises cholesterol.

8. The method of claim 1, wherein the lipid comprises cholesterol and a phosphatidylcholine having two acyl chains and wherein each of the acyl chains is at least 16 carbon atoms in length.

9. The method of claim 1, wherein the concentration of the lipid in the micellar suspension is at least 4 mg/ml.

10. The method of claim 1, wherein the detergent inhibits the endotoxin assay by a factor of at most about 50.

11. The method of claim 10, wherein the detergent inhibits the assay by a factor of at most about 10.

12. The method of claim 11, wherein the detergent inhibits the assay by a factor of at most about 1.

13. The method of claim 1, wherein the detergent is a polyoxyethylene ether.

14. The method of claim 13, wherein the detergent is a polyoxyethylene ether having from about 6 to about 23 ethylene units.

15. The method of claim 14, wherein the detergent is a polyoxyethylene ether having 10 ethylene units.

16. The method of claim 1, wherein the concentration of the detergent in the micellar suspension is less than 1.5% (w/w).

17. The method of claim 16, wherein the concentration of the detergent in the micellar suspension is about 0.5%.

18. The method of claim 1, wherein the assay is a Limulus amebocyte Iysate assay.

19. The method of claim 1, wherein the lipid comprises a phosphatidylcholine having two acyl chains, each of the acyl chains is at least about 16 carbon atoms in length, the lipid concentration in the micellar suspension is at least about 4 mg/ml, the detergent is polyoxyethylene 10 lauryl ether, the detergent concentration in the micellar suspension is less than 1.5% (w/w), the assay is a Limulus amebocyte Iysate assay, and the detergent inhibits the assay by at most a factor of about 2.5.

20. The method of claim 1, wherein the liposome further comprises a bioactive agent.

* * * * *